US012721894B2

(12) United States Patent
Mallozzi

(10) Patent No.: US 12,721,894 B2
(45) Date of Patent: Sep. 1, 2026

(54) METHOD AND SYSTEM FOR APPLYING PULSED ELECTRIC FIELDS WITH HIGH UNIFORMITY USING CHARGED RING STRUCTURES

(71) Applicant: The Phantom Laboratory, Incorporated, Salem, NY (US)

(72) Inventor: Richard Mallozzi, Middleton, MA (US)

(73) Assignee: The Phantom Laboratory, Incorporated, Salem, NY (US)

( * ) Notice: Subject to any disclaimer, the term of this patent is extended or adjusted under 35 U.S.C. 154(b) by 1033 days.

(21) Appl. No.: 17/797,979

(22) PCT Filed: Feb. 4, 2021

(86) PCT No.: PCT/US2021/016554

§ 371 (c)(1),
(2) Date: Aug. 5, 2022

(87) PCT Pub. No.: WO2021/158746

PCT Pub. Date: Aug. 12, 2021

(65) Prior Publication Data

US 2023/0075948 A1 Mar. 9, 2023

Related U.S. Application Data

(60) Provisional application No. 63/143,303, filed on Jan. 29, 2021, provisional application No. 62/971,562, filed on Feb. 7, 2020.

(51) Int. Cl.
*A61K 41/00* (2020.01)
*A61K 31/7048* (2006.01)
(Continued)

(52) U.S. Cl.
CPC ...... *A61K 41/0028* (2013.01); *A61K 31/7048* (2013.01); *A61N 1/40* (2013.01); *A61P 35/00* (2018.01)

(58) Field of Classification Search
CPC . A61K 41/0028; A61K 31/7048; A61P 35/00; A61N 1/40; A61N 1/28; A61N 1/36002; A61B 2018/1407
(Continued)

(56) References Cited

U.S. PATENT DOCUMENTS 4,822,470 A 4/1989 Chang
8,019,414 B2 * 9/2011 Palti .................. A61K 41/0052 607/3
(Continued)

FOREIGN PATENT DOCUMENTS

JP 3677540 B2 8/2005
WO 2019018207 A1 1/2019
WO WO-2020117662 A1 * 6/2020 .............. A61N 2/02

OTHER PUBLICATIONS

Extended European Search Report issued in EP Application No. 21750028.9, mailed on Jan. 23, 2024, 8 pages.
(Continued)

*Primary Examiner* — Beverly M Flanagan
(74) *Attorney, Agent, or Firm* — Sung IP Law PLLC

(57) ABSTRACT

A device, system and method for generating pulsed electric fields with high uniformity are provided. The electric fields occupy a large volume, suitable for placing a human or animal patient. A device for generating the electric fields is provided, which comprises a plurality of ring structures made of an electrically conductive material, wherein the ring structures are charged to different voltage levels. The device generates an electric field of high uniformity in the interior region of the ring structures when pulsed with electrical currents. These electric field pulses, when used in conjunction with pharmacological agents, destroy cancer cells through a process called targeted osmotic lysis.

6 Claims, 7 Drawing Sheets

(51) Int. Cl.
*A61N 1/40* (2006.01)
*A61P 35/00* (2006.01)

(58) Field of Classification Search
USPC .......................................................... 606/32
See application file for complete search history.

(56) References Cited

U.S. PATENT DOCUMENTS

| | | | |
|---|---|---|---|
| 8,921,320 B2 | 12/2014 | Paul et al. | |
| 2004/0010290 A1* | 1/2004 | Schroeppel ............. | A61N 1/30 607/3 |
| 2008/0084210 A1 | 4/2008 | Vaughan et al. | |
| 2013/0184218 A1 | 7/2013 | Paul et al. | |
| 2014/0357936 A1 | 12/2014 | Simon et al. | |
| 2014/0375793 A1 | 12/2014 | Simon et al. | |
| 2019/0133683 A1 | 5/2019 | Matloubian et al. | |

OTHER PUBLICATIONS

Liu et al. 'On the Induced Electric Field Gradients in the Human Body for Magnetic Stimulation by Gradient Coils in MRI', IEEE Translations on Biomedical Engineering, vol. 50, issue 7, Jun. 20, 2003 (Jun. 20, 2003), p. 804-815.

International Search Report issued in WO Appln. No. 2021/158746 A1, mailed on May 18, 2021, 2 pages.

* cited by examiner

TOL - Digoxin Dose Frequency

% Change Cross-sectional Area (mm2)

100
50
0
-50
-100

TOL/Dig x 1
TOL/Dig x 3
TOL/Dig x 5
TOL/Dig x 8

-1
0
1
2

METHOD AND SYSTEM FOR APPLYING PULSED ELECTRIC FIELDS WITH HIGH UNIFORMITY USING CHARGED RING STRUCTURES

RELATED APPLICATION

This application is a § 371 National Stage Application of PCT/US2021/016554, filed Feb. 4, 2021, which claims priority benefit to U.S. Provisional Application No. 62,971,562, filed Feb. 7, 2020, and U.S. Provisional Application No. 63/143,303, filed Jan. 29, 2021, both of which are fully incorporated herein by reference for all purposes.

FIELD

The present invention relates to the field of medical device and medical treatment of diseases and disorders. More specifically, the invention concerns a method and system for generating pulsed electric fields with high uniformity via charged ring structures for medical applications.

BACKGROUND ART

Pulsed electric field treatment is now widely used in diverse biological and medical applications: gene delivery, electrochemotherapy, and cancer therapy. One advantage of pulsed electric field treatment is its ability to destroy tissues or tumors in a nonthermal manner. Consequently, pulsed electric field treatment makes it possible to preserve sensitive tissues intact, such as blood vessels and axons. Furthermore, this non-invasive technique allows the possibility of regeneration with healthy cells and tissues in the treatment region without leaving a scar.

A conventional appliance for generating pulsed electric fields consists of three parts: pulse generator, electrodes, and connection links between them. The pulse generator produces square wave pulses at regular intervals. Amplitude, pulse width, period, and phase delay are the primary parameters to determine the shape of the output waveform. Electric field strength, depending on the amplitude of the pulse and the distance between the electrodes, is often crucial for completed treatment effect. When electrodes are unsuitable, the strength in a certain target area is insufficient, resulting in incomplete treatment effects.

The conventional technique for generating electric fields that is similar to that used in radar has some drawbacks in costs and availability. A typical equipment using this technique is a bipolar generator that generates a short square wave and reverses polarity, in part to avoid erosion of electrodes. However, a bipolar generator costs about twice as much as a monopolar one. Other wave forms include exponential decay and sinusoidal. The sinusoidal form is somewhat easier to generate, as it uses equipment similar to common radio equipment, but it reaches its peak power only for an instant and thus delivers less energy per cycle above the critical field strength than does a square wave.

Three alternative techniques currently exist for generating electric field pulses. In one technique, the electric field is created between two large conducting plates, each of which is charged so that there is a voltage difference between the plates. A patient is placed between the plates. The electric field points from one plate to the other and is oriented perpendicularly to a large portion of the patient's surface area, which leads to substantial reductions of the electric field inside the patient. This makes it very difficult to control the field inside the patient, because the actual field will be very sensitive to the percentage of the space between the plates that is filled by the patient. The resulting field will vary substantially with patient's weight. The field may also vary within the patient's anatomy as the local anatomy fills more or less of the region between the plates. For instance, in a patient with a large abdomen, the field in the abdomen would be quite different from in the chest or head of the patient. The conducting plates could be placed directly in contact with the patient to avoid field variation. However, typical conducting plates may only contact a small portion of the patient's skin unless they are flexible.

Another technique that has been applied in laboratory experiments is to use a solenoidal coil with an empty bore, inside which the patient is placed. The current in the coil is ramped in time, leading to a changing magnetic field, which by Faraday's Law of Induction creates a changing electric field inside the patient. The coil is made out of magnetic materials. One disadvantage of this technique is the spatial variation in the electric field produced by a solenoidal coil, which is zero along the center axis and increases with radius from the axis. Furthermore, the power requirements are extremely high if scaled up to a human or large-animal-sized device, with peak powers in the range of 50-400 kilowatts. Such high power requirements present a large challenge for building facilities. This technique also requires extremely powerful heat removal systems from both the device itself and the building in which the device operates. The electrostatic ring unit produces heat comparable to other small appliances such as light bulbs.

A third technique is to create the electric field by ramping a magnetic field inside materials with high magnetic susceptibility. The electric field produced in this manner has the desirable properties, but the device can weigh a large amount due to the large quantities of magnetic material required. An additional drawback of this technique is that the upper limit of the electric field strength for a given pulse duration is limited by the material properties of the magnetic material.

Although advances have been made recently in the use of electric pulses to induce cell death, there still remains a need in the art for improved devices and methods for destroying diseased or disordered tissues, such as tumor tissues, without damaging normal tissues. Especially there is a need for devices and methods of generating pulsed electric fields in large volumes with high uniformity.

SUMMARY OF THE INVENTION

In view of the foregoing, the object of the present invention is to address the need for generating pulsed electric fields (PEFs) in large volumes with high uniformity for medical applications. Embodiments of the present invention pertain to devices and methods for creating pulsed electric fields for a human or animal subject as part of a cancer treatment protocol. The present invention provides a system to generate electric fields with a large volume and high uniformity that are suitable for placing a human or animal patient inside.

An embodiment is described for a device for generating pulsed electric fields that comprises a plurality of coaxial, electrically conductive ring structures. The ring structures are large enough to place a human or animal subject in their interior region and separated by distances in the range of a few inches to a few feet. Each ring structure is charged to a voltage level; the voltage difference between the ring structures gives rise to an electric field in the interior region. The voltage levels applied to each ring structure are designed to optimize the uniformity of the electric field produced. According to one embodiment, the electric field is applied as a series of repeated pulses.

Another embodiment is described of a system comprising the electrically conductive ring structures connected to a set of driving electronics that allows a user to control the amplitude, duration, and spacing of the electrical field pulses. The driving electronics include components to generate pulsed voltage or current waveforms, components to amplify and filter the output of the waveforms, and a microprocessor that presents a user interface for controlling the output.

The device and system for generating the electric field according to the present invention possess various desirable features. First, the electric field generated has high spatial uniformity. Second, the electric field points tangentially to the surface of a patient lying in the device. Third, the power requirements and heat generation are very low relative to some other methods. Fourth, the driving electronics are relatively simple. Fifth, the present device is lightweight by nature.

The electric field pulses generated by the present invention, when used in conjunction with a pharmacological agent, may destroy cancer cells through a process called targeted osmotic lysis (TOL) as described in U.S. Pat. No. 8,921,320, the entire disclosure of which is expressly incorporated herein by reference.

Another embodiment provides a method for therapeutic treatments via targeted osmotic lysis, comprising administering to a human or animal subject in need a therapeutically effective dose of pulsed electric fields stimulation generated by the device and system according to the present invention. This method can be used in the application of targeted osmotic lysis for treating cancers when combined with a pharmacological agent for blocking a Na+, K+ ATPase. In some embodiments, a method for therapeutic treatments via targeted osmotic lysis comprising administering a therapeutically effective dose of pulsed electric fields monthly to a human or animal subject with a tumor for life or until the tumor is clinically undetectable.

BRIEF DESCRIPTION OF THE DRAWINGS

The invention will be described in more detail below on the basis of one or more drawings, which illustrates exemplary embodiments.

DETAILED DESCRIPTION OF THE EMBODIMENTS

It should be understood that this invention is not limited to the particular methodology, protocols, and systems, etc., described herein and as such may vary. The terminology used herein is for the purpose of describing particular embodiments only and is not intended to limit the scope of the present invention, which is defined solely by the claims.

As used in the specification and appended claims, unless specified to the contrary, the following terms have the meaning indicated below.

"Tumor" as used herein refers to all neoplastic cell growth and proliferation, whether malignant or benign, and all precancerous and cancerous cells and tissues.

"Cancer" and "cancerous" relate to or describe the physiological condition in mammals that is typically characterized by unregulated cell growth. Benign and malignant as well as dormant tumors or microwound metastases are included in this definition.

"Subject" means a mammal, such as, but not limited to, a human or non-human mammal, such as a cow, equine, dog, sheep or cat.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments.

This invention addresses a need to create pulsed electric fields in large (human-body-sized) volumes. This need arises within the application of targeted osmotic lysis (TOL), which uses such electric field pulses to stimulate sodium channels in the cell membrane of cancer cells to open. See U.S. Pat. No. 8,921,320. It is desirable to have the electric field highly uniform so that the associated therapeutic effect will be uniform.

Figure 1:
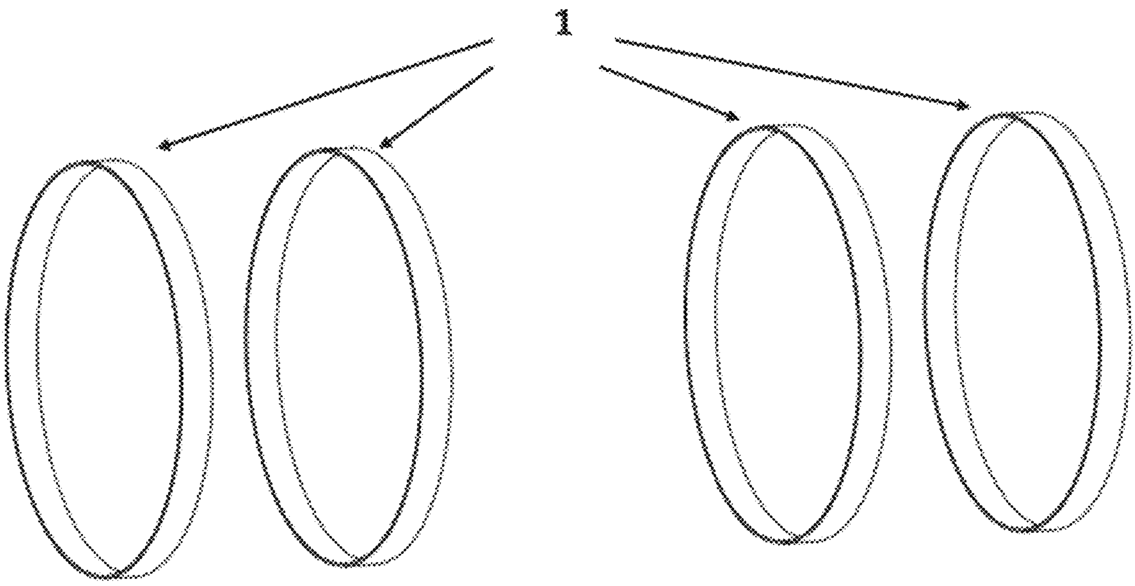
FIG. 1 shows a plurality of ring structures arranged coaxially to provide an extended region of electric field exposure.

The electrical field is produced by the voltage differences between the ring structures, as depicted in FIG. 1. Each ring structure has a voltage charged to it. The voltage difference between the ring structures gives rise to an electric field between the rings, which near the axis of the device is oriented predominantly along the axis. The values of the voltages applied to each ring structure, as well as the spatial location and diameter of the ring structures, are optimized to produce an electric field of the strength and uniformity desired.

The circular shape of the ring structures is a preferred embodiment, as they produce fields with good uniformity. It should also be appreciated that fields could be produced with non-circular shapes, including but not limited to, ellipses, polygons, and rectangular shapes. The ring structures do not necessarily have the same diameter.

The ring structure may be made of an electrically conductive material including, but not limited to, metals, electrolytes, superconductors, semiconductors, plasmas and some nonmetallic material such as graphite and conductive polymers.

By using a multiplicity of such ring structures with different voltage levels and carefully-designed geometrical relationships with regard to diameter, large regions of high-electric-field uniformity can be generated. In this arrangement as depicted in FIG. 1, a plurality of the ring structures (1) are aligned so they share a common axis, and spatially separated by a distance. In this arrangement, the patient is placed along the central axis of the device. When arranged as such, the electric field generated runs along the axis of the ring structures, which would, in the preferred application, run along the long axis of a human patient or many types of veterinary patients. Larger regions of uniformity can be created by increasing the number of ring structures. Such designs can extend to arbitrarily large numbers of ring structures to increase the homogeneous volume, at the expense of system cost, weight, and complexity.

To obtain electric field pulses of a given amplitude, each ring structure is charged to a voltage level; the voltage difference between the ring structures gives rise to an electric field in the interior region.

Figure 2:
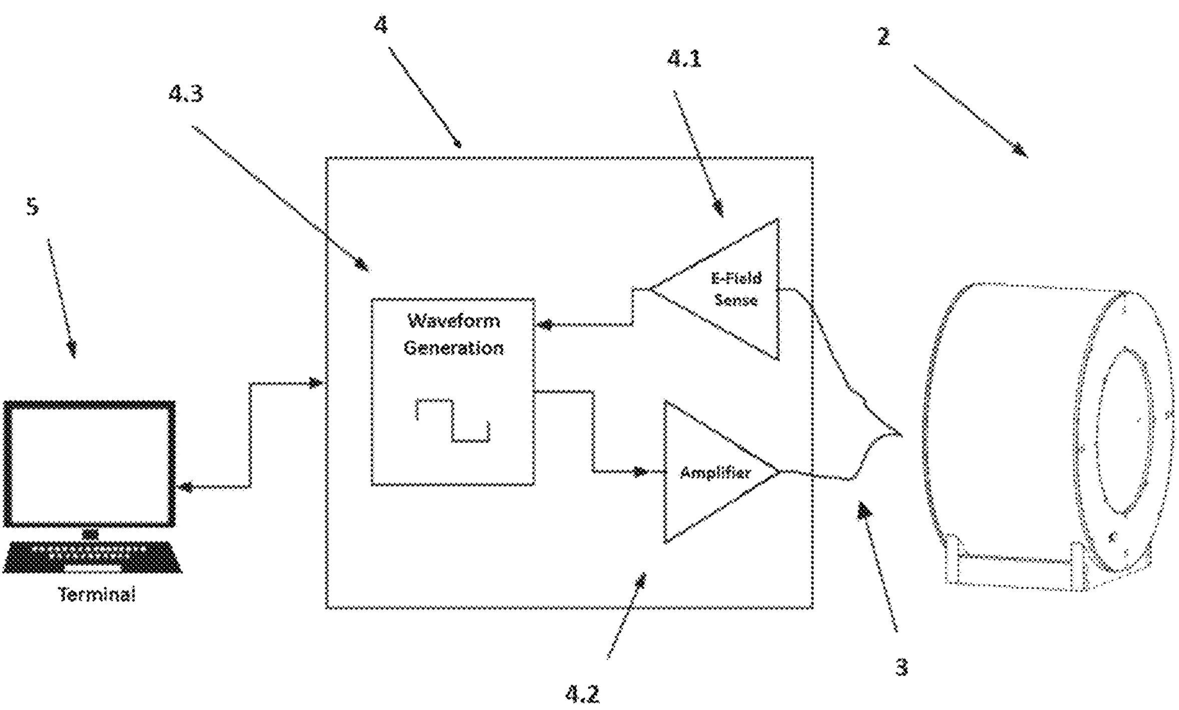
FIG. 2 shows a system comprising an electronic ring unit in an enclosure and connected to a control system for application of therapy involving electric fields.

The device creating the electric field can further be incorporated into a system that can be applied in a therapeutic capacity that, when combined with pharmacological agents, can treat some types of cancers. Specifically, the system comprises one or more rings in an enclosure, called electrostatic ring unit (ERU), and connected to a control system for application of therapy involving electric fields. FIG. 2 shows the block diagram of the system. The electrostatic ring unit (ERU) (2) produces electric field pulses in the interior region, where a patient is placed. Cables (3) connect the electrostatic ring unit to driving and sensing circuitry (4) that provide voltage or current pulses to the rings in the ERU (2). Sensing coils inside the ERU measure the electric field produced inside and can be used to control the output. A microprocessor (5) presents a user interface to the operator of the device, and interfaces to the driving and sensing circuitry to control the amplitude, duration, and spacing of the pulse, as well as to start and stop the pulses.

The driving electronics are connected to a computer that hosts a user interface that enables the user to control the pulse amplitude, duration, and spacing, as well as starting and stopping the pulse therapy. The computer can communicate with the driving electronics through a serial bus, though other choices are possible.

The electric field amplitude can be controlled by electric field sensors (4.1) in an 'open-loop' arrangement, in which the expected electric field output is known from the input voltage, the currents created, or in a 'closed-loop' arrangement in which a feedback loop is used. The feedback could come in multiple forms, such as measuring the actual voltage applied to each ring, or from an electric field sensor inside the device that measures the electric field applied.

The voltage pulses in the driving electronics can be created with many different types of amplifier configurations (4.2). Since it is usually desirable to have voltages driving the rings in the range of 15-100 Volts, a Class D amplifier configuration is desirable to avoid large heat dissipation in the output transistors of the amplifier. This configuration uses Pulse Width Modulation (PWM) to control the output of the amplifier and is known for its high efficiency and low cost.

One important property of the electric field produced by the present invention is high uniformity. High uniformity is desirable so that the therapy is applied in a manner consistent throughout the body or region of treatment. The usable therapeutic region for this application is where the field strength variation is less than approximately 10% in empty space.

Another important aspect of the present invention is that the electric field points tangentially to the surface of a patient lying in the device. The desirability of the electric field pointing tangentially to the surface of the patient stems from the need to minimize the reduction in electric field that occurs from polarized water molecules inside the body. Water has a very strong polarizability (electric susceptibility), which leads to a large reduction in field inside the body. This effect is maximized in fields that point perpendicular to the surface, with reductions in electric fields as high as a factor of 75-80. For electric fields pointing along the surface of the patient, the reduction can be far smaller, ranging from almost no reduction to a reduction by a factor of approximately 20.

Still another important aspect of the present invention is that the device produces the electric fields with very low power generated, leading to low-cost driving electronics, low electrical requirements for a facility, and no impact on the HVAC systems of a clinical facility. Furthermore, the device is lightweight by nature.

The pulsed electric field system can be applied in a therapeutic technique called Targeted Osmotic Lysis (TOL). See U.S. Pat. No. 8,921,320. The principle behind the technique is that the electric field pulses stimulate sodium channels in the cell membrane to open, passing more sodium into the cell. Cancer cells are known to have far more sodium channels than non-cancer cells. The treatment of electric field pulses stimulates sodium channels and results in an increase in sodium concentration inside the cancer cell, which leads to a subsequent influx of water, causing the cancer cell to rupture. The normal tissue remains intact in this treatment.

A pharmacological agent for blocking the exit of the sodium from the cell, such as a $Na^+$, $K^+$-ATPase blocker, may be used together with pulsed electric fields to enhance the therapeutic efficacy. Non-limiting examples of pharmaceutical compounds that can be used to block Na+, K+ ATPase include ouabain (g Strophantin); dihydroouabain; ouabain octahydrate; ouabagenin; digoxin; digitoxin; digitalis; acetyldigitoxin; acetyldigoxin; lanatoside C; deslanoside; metildigoxin; gitoformate; oleanderin; oleandrigenin; bufotoxin; bufotalin; marinobufagenin (3,5 dihydroxy 14,15 epoxy bufodienolide); palytoxin; oligomycins A, B, C, E, F, and G; rutamycin (oligomycin D); rutamycin B; strophanthin (g strophanthin, Acocantherine); k β strophanthin; strophanthidin; k strophanthoside; cymarin; erysimoside (cardenolide); helveticoside; peruvoside; hypothalamic Na+, K+ ATPase inhibitory factorn (HIF); the aglycone of HIF; arenobufagin; cinobufagin; marinobufagin; proscillaridin; scilliroside; daigremontianin; 3, 4, 5, 6, tetrahydroxyxanthone; and all other inhibitors of Na+, K+ ATPase, combinations and derivatives of each.

The Na+, K+ ATPase blocker may be delivered to a single tumor via direct or intravenous administration, to a single organ or area via intravenous or intraluminal administration, or the entire body via intravenous, subcutaneous, intramuscular or oral administration. Pulsed electric field stimulation of sodium channels can be delivered to a single tumor, a single organ, a section of the body, or the entire body. All types and subtypes of the VGSCs family should be equally susceptible to this technology. For example, cell lines that over-express Nav1.1, Nav1.2, Nav1.3, Nav1.4, Nav1.5, Nav1.5n, Nav1.6, Nav1.7, Nav1.8 and Nav1.9 are susceptible to mediated targeted lysis.

Figure 3:
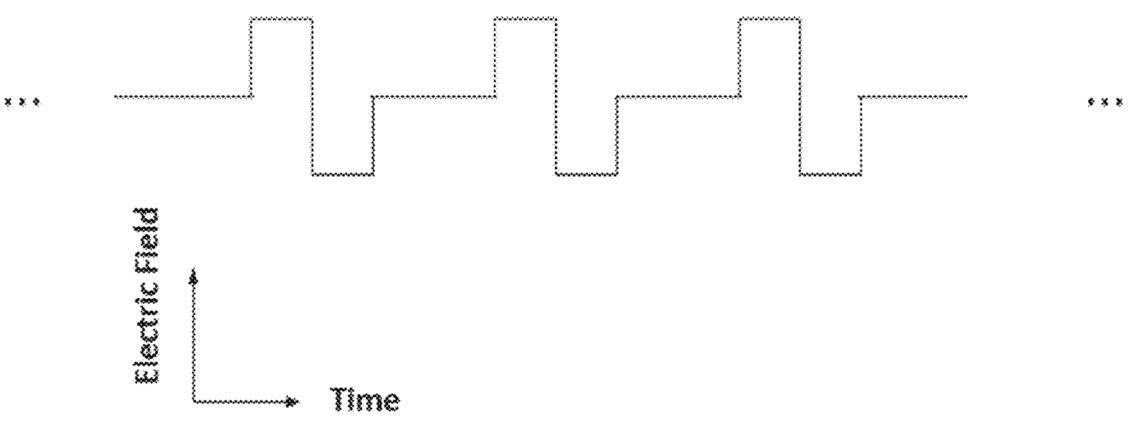
FIG. 3 shows a typical pulse train associated with the TOL application.

FIG. 3 shows a typical pulse train associated with the TOL application. The electric field amplitude falls in the range of 0.1 V/m to 100 V/m in free space. The pulses consist of a forward polarization of approximately 1-50 milliseconds, followed by a reverse polarization of similar duration and amplitude. The pulses are separated by 5-50 milliseconds from finish to start. The precise details of timing, duration, and amplitude may vary widely in the application.

Figure 4:
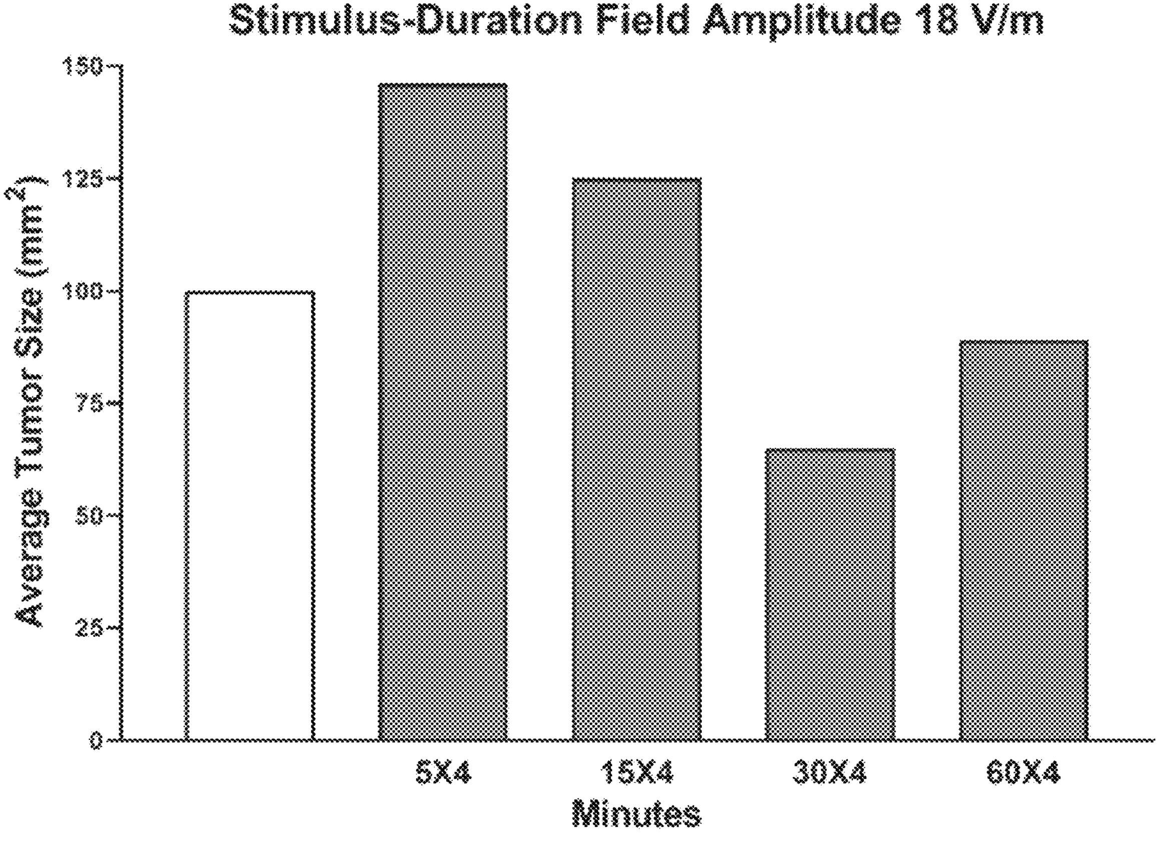
FIG. 4 shows a stimulus duration-response curve for pulsed electric fields within a single day of treatment.

FIG. 4 illustrates the average size of 4T1 homographs seen before and after each single treatment with TOL in which the duration of each of four exposures to PEFs of 18 V/m varied from 5-60 minutes (n=15). As shown in FIG. 4, a reduction in the average tumor size from baseline was observed when exposures of 30 minutes were provided. Further increase in stimulation duration had less of an effect on tumor reduction. Optimum tumor reduction is observed when the mice are exposed to a PEF for 30 minutes, or a range of exceeding 15 minutes and less than 60 minutes.

Figures 5A, 5B, 5C:
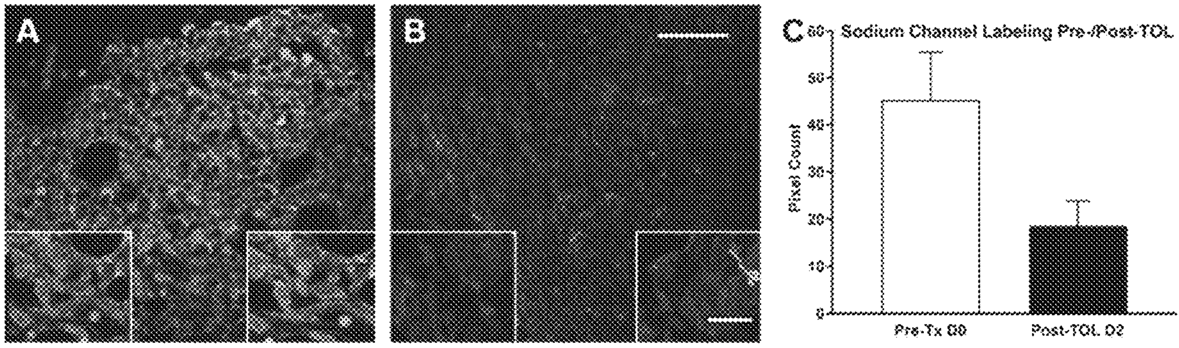
FIGS. 5A-5C show sodium channel labeling of voltage-gated sodium channel (VGSC) in 4T1 homografts before and after treatment with TOL.

FIGS. 5A-5C depict the immunohistochemical labeling of voltage gated sodium channel (VGSC) in 4T1 homografts before (FIG. 5A) and after (FIG. 5B) a single 2-day treatment with TOL. Nuclei are counterstained with DRAQ5™ fluorescent probe. The number of cells that highly express VGSCs decreases significantly following treatment with TOL potentially contributing to the lack of continued tumor reduction with treatments beyond day 2. Low power calibration bar in FIG. 5B is 50 μm and the high power calibration bar in the inset is 25 μm. The histogram in FIG. 5C depicts the pixel counts that represent sodium channel expression revealed in homografts before and after treatment with TOL. As shown in FIG. 5C, TOL eliminates virtually all of the neoplastic cells in solid tumors that most highly express VGSC. This observation may explain, in part the loss of TOL's efficacy that is observed after the first 2 days of treatment.

Figure 6:
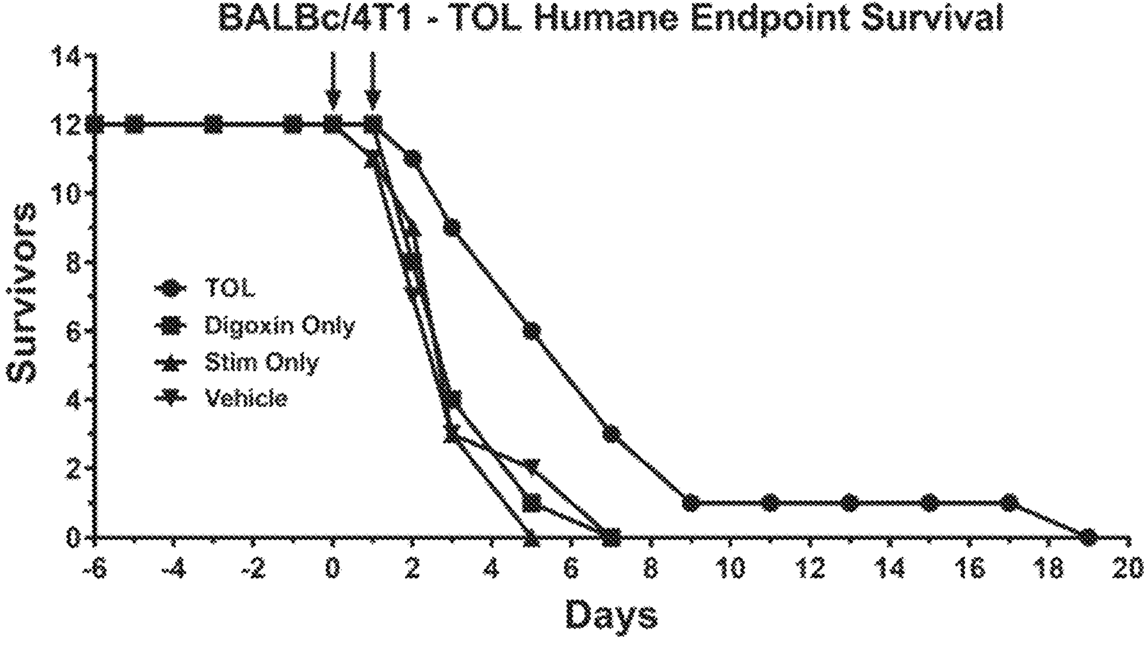
FIG. 6 shows post-treatment survival in a triple negative breast cancer mouse model receiving TOL.

FIG. 6 depicts in vivo validation of the therapeutic efficacy of pulsed electric fields (PEFs) inducing osmotic lysis in a breast cancer mouse model. Ectopic homografts of 4T1 murine breast cancer cells were established in female, immune competent BALBc mice (n=12). The "TOL" group was injected with digoxin (7 mg/kg) and then exposed to the PEFs generated by a ring device. This treatment was administered on day 0 (first day of treatment), and on day 1. The "Drug Only" group received digoxin (7 mg/kg) only, the "Stim Only" group received PMFs stimulation only, and the "Vehicle" group received 10% DMSO/saline only. Treatment with TOL and controls was administered on 2 successive days (arrows). Tumor size was measured daily, beginning on Day 0 (first day of treatment) and every other day after Day 3 until NIH humane endpoint criteria were met for euthanasia. As shown in FIG. 4, treatment with TOL significantly extends the post-inoculation period needed to meet humane endpoint criteria compared to that seen in the groups of control-treated mice. TOL significantly increases survival of murine hosts compared to negative treatment controls without adversely affecting behavior or producing tissue injury.

Figure 7:
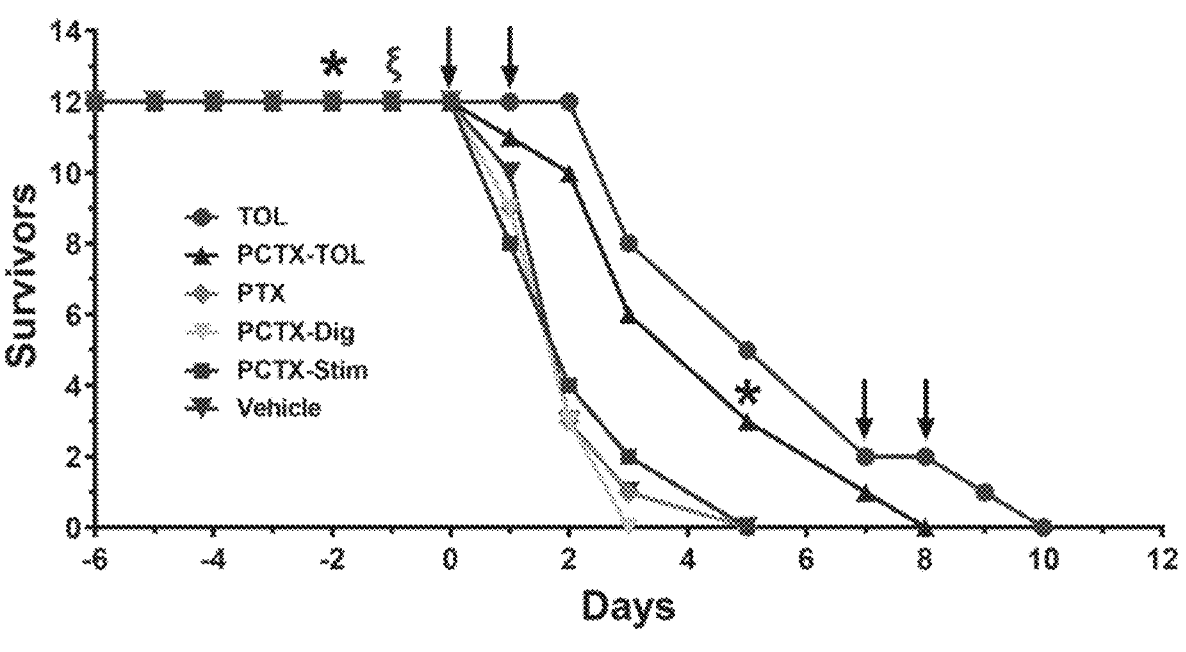
FIG. 7 shows post-treatment survival in a triple negative breast cancer mouse model receiving TOL or paclitaxel.

FIG. 7 depicts in vivo validation of the therapeutic efficacy of pulsed electric fields (PEFs) inducing osmotic lysis in comparison to paclitaxel in a breast cancer mouse model. Paclitaxel is currently the best chemotherapy for triple negative breast cancer. Ectopic homografts of 4T1 murine breast cancer cells were established in female, immune competent BALBc mice (n=12) and were subjected to different treatments. FIG. 7 illustrates the number of days that transpired between the inoculation of BALB/c mice with 4T1 murine breast cancer cells and when the homografts met criteria for humane endpoint euthanasia. Five days after inoculation, mice received either a single, 20 mg/kg i.p. dose of paclitaxel (black diamonds) or an equal volume of vehicle used to suspend the paclitaxel (black inverted triangles). Csi (ξ) denotes the day paclitaxel and paclitaxel vehicle was administered. Additional control groups received 20 mg/kg paclitaxel on post-inoculation day 5 and then received either eight 3 mg/kg doses of digoxin (Dig) or four 30-minute periods of stimulation (Stim) with PEF (18 V/m field amplitude, a 10 ms positive/negative ramp and a 15 ms interstimulus interval) on 2 successive days (arrows) as controls for treatment with paclitaxel and TOL. Homografts were measured on post-inoculation day 6 (treatment day 0), and again on post-treatment days 1 and 2 and then every other day until the criteria for humane endpoint euthanasia was met. As shown in FIG. 7, treatment with paclitaxel had no significant effect on survival over controls. The time needed to meet humane endpoint euthanasia for mice treated with TOL alone was significantly increased over PCTX alone and controls, but combining paclitaxel with TOL reduced the effect provided by TOL alone. Thus, TOL significantly increases survival of murine hosts compared with mice treated with paclitaxel, a positive control for the treatment of triple-negative breast cancer. Concurrent treatment with TOL and paclitaxel reduces the effectiveness of TOL. The decrease in the effectiveness of TOL in the concurrent treatment with paclitaxel may be possibly due to a decrease in the expression of VGSC of tumor cells attributed to the treatment of paclitaxel as described below in FIGS. 8A-8D.

Figures 8A, 8B, 8C, 8D:
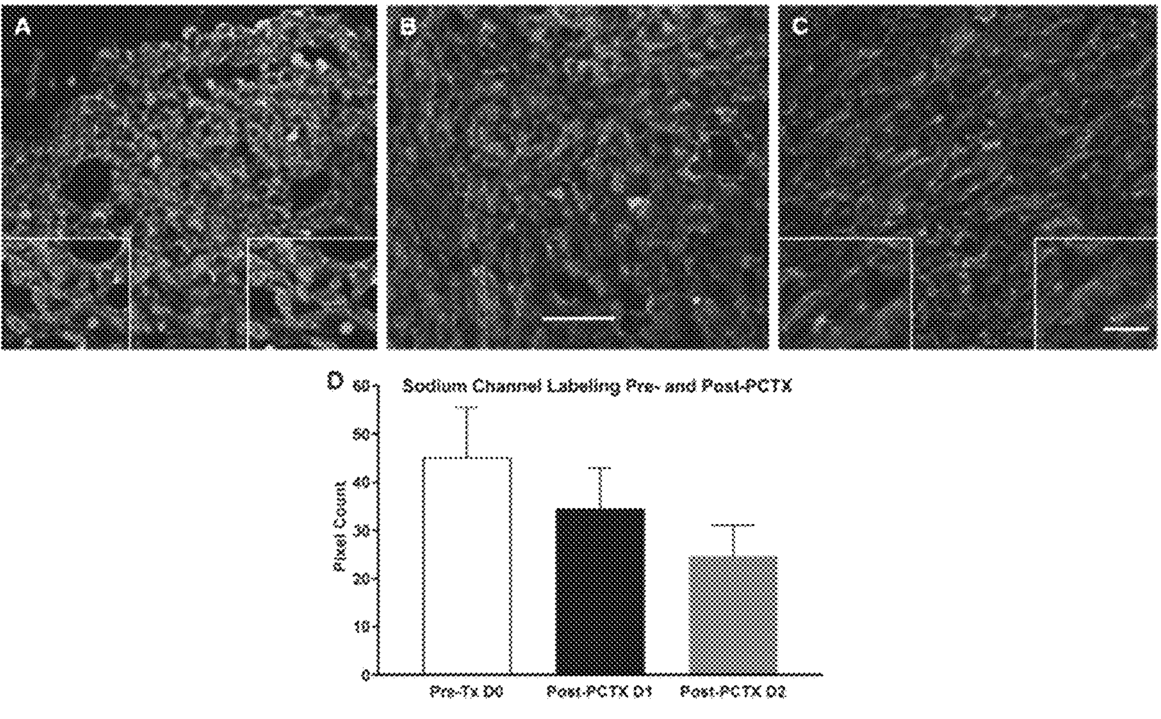
FIGS. 8A-8D show sodium channel labeling of VGSC in 4T1 homografts before and after treatment with paclitaxel.

FIGS. 8A-8D depicts the immunohistochemical labeling of VGSC in 4T1 homografts before (FIG. 8A), 1 (FIG. 8B) and 2 days (FIG. 8C) after treating with paclitaxel. Nuclei are counterstained with DRAQ5. The VGSC expression decreases significantly and progressively following the initiation of treatment with paclitaxel. Low power calibration bar in FIG. 8B is 50 μm and the high power calibration bar in the inset in FIG. 8C is 25 μm. The histogram in FIG. 8D shows the pixel counts that represent sodium channel expression revealed in homografts before and 1 (FIG. 8B) and 2 days (FIG. 8C) after treatment with paclitaxel. It is noted that there is a progressive reduction of VGSC labeling but not in the number of cells that express the highest levels of VGSC. These data indicate that Paclitaxel decreases the expression of VGSC in 4T1 murine breast cancer homografts. The decrease in expression of VGSC is likely to contribute in the reduced efficacy of TOL when used concurrently with paclitaxel.

Figures 9, 10:
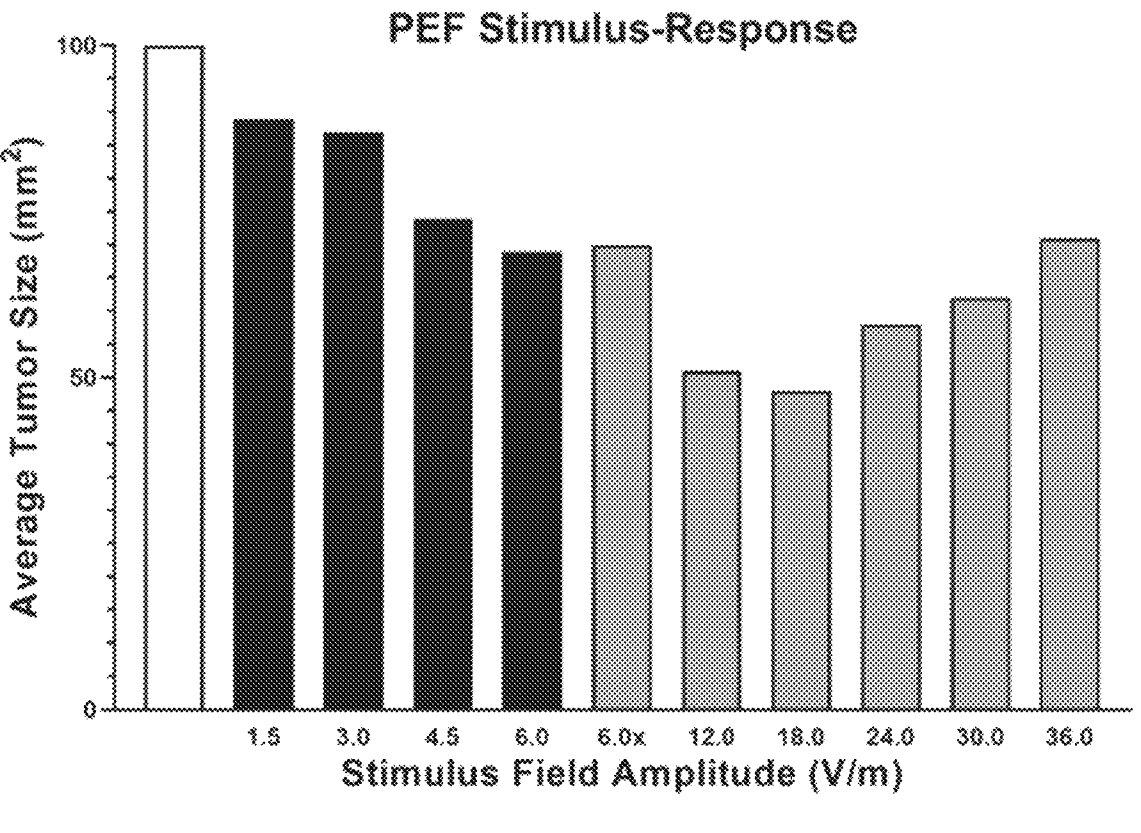
FIG. 9 shows the differences in reducing tumor size in ectopic 4T1 homografts mice between the toroid device and ring device.
FIG. 10 shows the effect of digoxin dosing frequency on the effect of TOL on reducing the size of homografts.

FIG. 9 depicts the reduction in average area of tumor in female, immune competent BALBc mice with ectopic homografts of 4T1 murine breast cancer cells receiving TOL using two types of pulsed electric field generating devices. The mice were subjected to pulsed electric fields at different voltage levels generating using three stimulating devices, two toroidal design (black bars) and one coaxial ring design (grey bars) due to the maximum field strength available for each device; 3.0 V/m and 6.0 V/m for the toroid devices, respectively, and 36.0 V/m for the coaxial ring device. The toroid devices used in this experiment are described in WO2020/117662. The coaxial ring device used is described herein in this present application. The bar graph summarizes the average tumor reduction observed following single treatments with TOL obtained with varying PEF strength compared to normalized baseline averages (white bar). It is noted that tumor reduction using the toroid device and coaxial ring device was comparable when PEFs at a field amplitude of 6V/m were delivered with either device (bars 6.0 and 6.0×) (n=8 for each stimulus group). As shown in FIG. 9, TOL-treatment with the coaxial ring device was maximally effective at a field amplitude of 18 V/m and less effective at field strengths of greater or lesser intensity.

FIG. 10 shows the effect of digoxin dosing frequency on the effect of TOL on reducing the size of homografts. The graph illustrates the difference in average reduction of 4T1 homograft size seen after treatment with TOL when steady-state levels of digoxin are neither achieved nor maintained. In this study, female murine BALBc mice received 1, 3, 5 (steady-state) or 8 (maintained steady-state) subcutaneous (s.c.) injections of digoxin (3 mg/kg) and 4×30-minutes exposures to pulsed electric field (PEF) stimulation (18 V/m, 10 ms positive/negative ramp, 15 interstimulus intervals) hourly for a total of 2 hours of stimulation on two sequential days (empty arrows). As shown in FIG. 10, when digoxin dosing frequency yielded less than 3 mg/kg steady-state levels of drug (filled triangles and diamonds), the additional exposure to PEFs had little effect on tumor growth. By contrast, when steady-state levels of digoxin were achieved (filled squares and circles), the exposure to PEFs resulted in a reduction of the size of homografts. The anti-tumor effect was improved when the steady-state levels of drug were maintained (filled circles). Thus, tumor reduction in response to treatment with TOL requires that a steady-state level of digoxin is attained prior to PEF stimulation. Efficacy can be improved if the steady-state level of digoxin is maintained throughout the period of stimulation.

Figure 11:
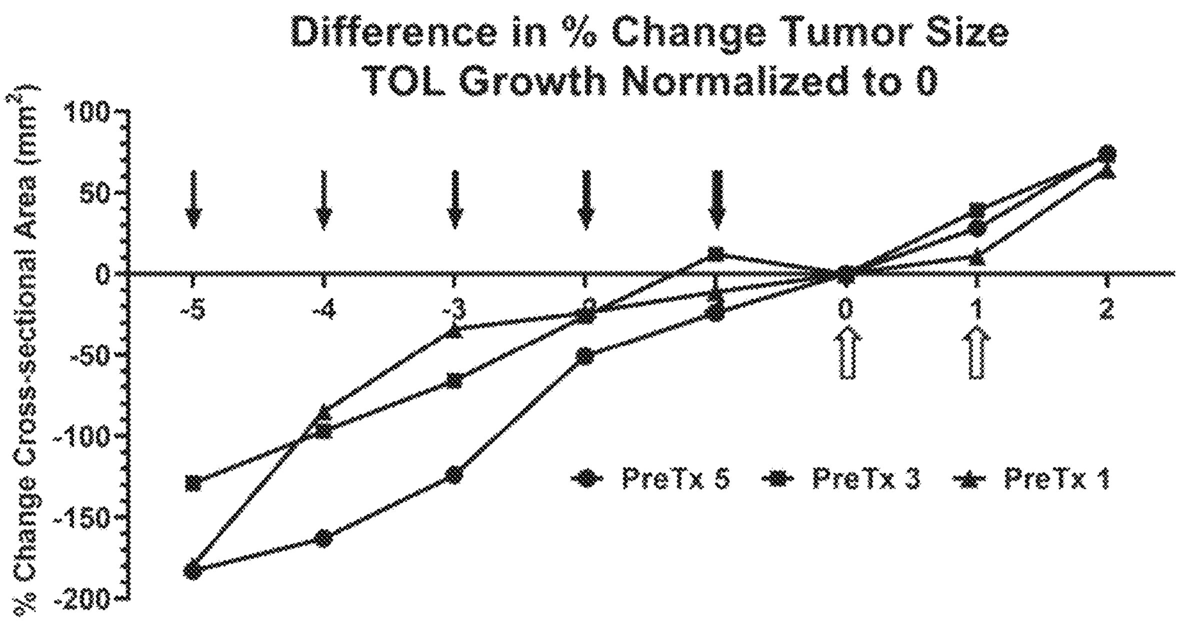
FIG. 11 shows the effect of TOL on growth of 4T1 homografts in female BALBc mice dosed to steady-state with digoxin prior to treatment with TOL.

FIG. 11 shows the effect of TOL on growth of 4T1 homografts in female BALBc mice dosed to steady-state (5 s.c. injections) with digoxin (3 mg/kg) for 1, 3 or 5 days (black arrows) prior to treatment with TOL (empty arrows). Although growth continued in all groups (n=6), the effect of TOL on the growth of homografts seemed to be least affected in the mice that were pre-treated for only 1 day (filled triangles) prior to being treated with TOL. Thus, daily pre-treatment of murine mice with digoxin sufficient to attain steady-state levels of the drug for as little as 1 day may eliminate TOL's effectiveness in reducing tumor size in a dose dependent fashion.

Figure 12:
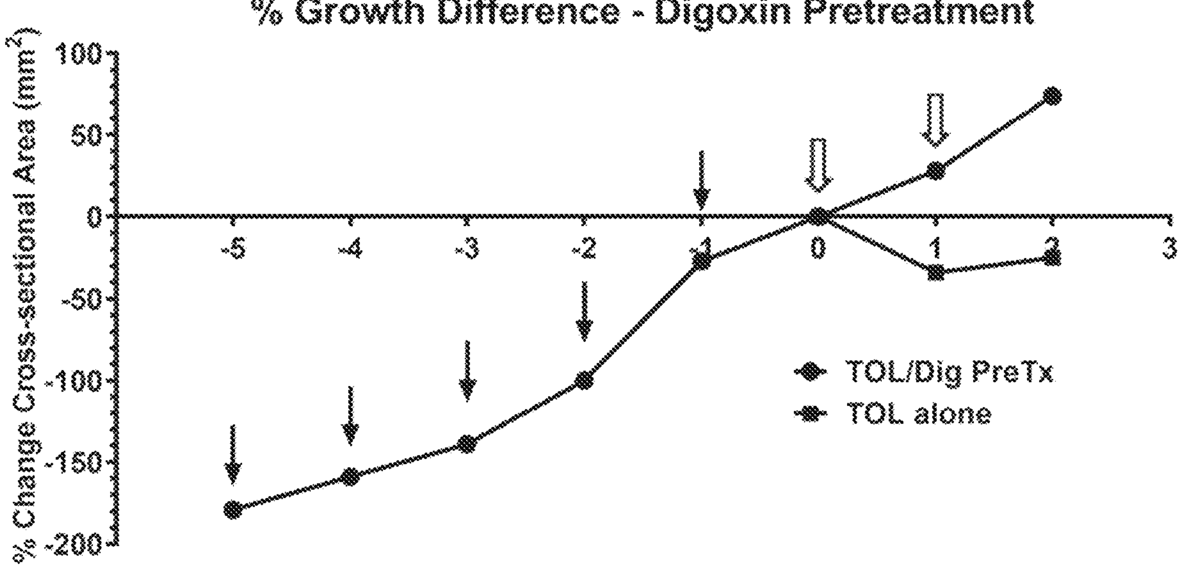
FIG. 12 shows the comparison of the effect of TOL on growth of 4T1 homografts in female BALBc mice with and without pretreatment of digoxin.

FIG. 12 shows the comparison of the effect of TOL on growth of 4T1 homografts in female BALBc mice dosed daily to steady-state (5 s.c. injections) with digoxin (3 mg/kg) pre-treated for 5 days (black arrows) with the growth of homografts in mice that were not pre-treated with digoxin prior to treatment with TOL (empty arrows). It is noted that the treatment with TOL without digoxin pretreatment decreases the size of homografts by approximately 40% (filled squares) but has no effect on the growth of homografts in mice that were pre-treated with digoxin (filled circles). Therefore, daily pre-treatment of murine mice with digoxin sufficient to attain steady-state levels of the drug may decrease the effectiveness of the TOL treatment in reducing tumor size.

Figure 13:
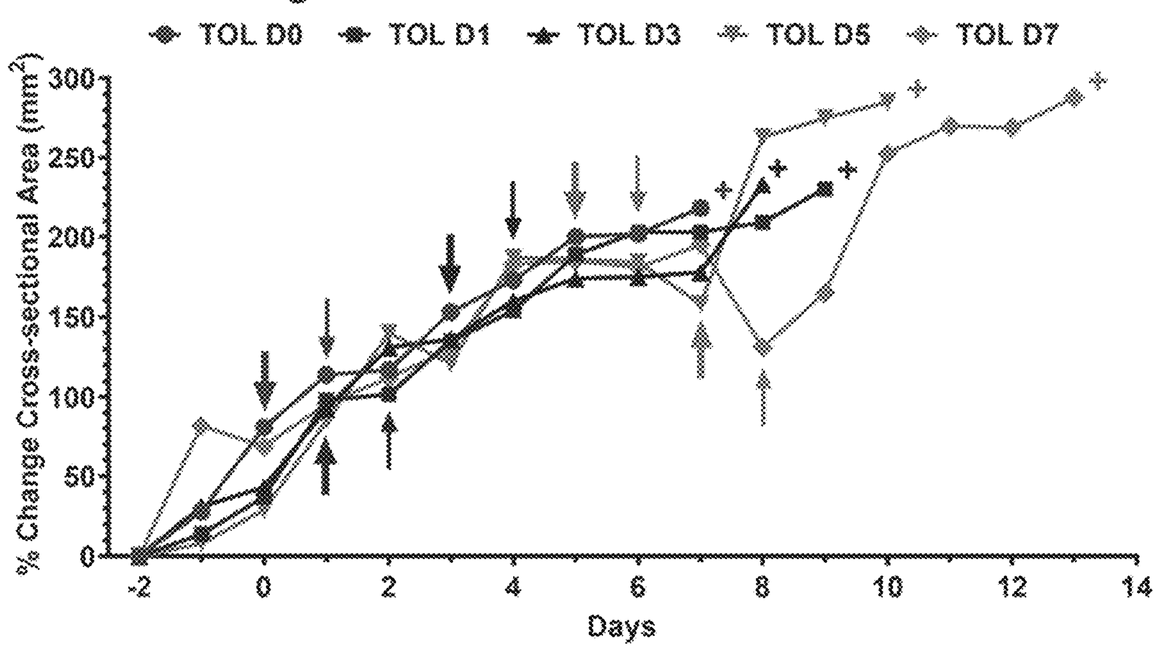
FIG. 13 illustrates the efficacy of the TOL treatment with different treatment interval between digoxin and PEF stimulation.

FIG. 13 illustrates the efficacy of the TOL treatment with different treatment interval between digoxin and PEF stimulation. Ectopic homografts of 4T1 murine breast cancer cells were established in female, immune competent BALBc mice. These mice received 5 injections of digoxin (3 mg/kg) to achieve steady-state levels on 2 sequential days. Groups of mice (n=12) were then treated at 0, 1, 3, 5 and 7 day intervals after the 2-day pre-treatment with TOL (8 s.c. injections of digoxin (3 mg/kg) administered hourly to achieve and maintain steady-state through 4×30-minutes exposures to pulsed electric field (PEF) stimulation (18 V/m, 10 ms positive/negative ramp, 15 interstimulus intervals for a total of 2 hours of stimulation on 2 sequential days)). No effect on the growth of homografts was observe within 5 days of the digoxin pre-treatment. A stepwise improvement in tumor reduction was observed when TOL was administered 5 and 7 days following digoxin pre-treatment. Plus signs (+) denote the day all mice in a group met humane endpoint euthanasia criteria. Survival was observed to be extended in the groups of mice that were treated with TOL 5 and 7 days after pre-treatment with digoxin in an interval dependent fashion. The data indicate that the tolerance that develops to digoxin is reversible. It is required that there be a digoxin free period between each 2-day round of treatments of at least 5 and preferably 7 days in small animals such as mice. The digoxin free period between each 2-day round of pulsed electric fields administration is about two to four weeks in human patients or large animals such as cats or dogs.

Figure 14:
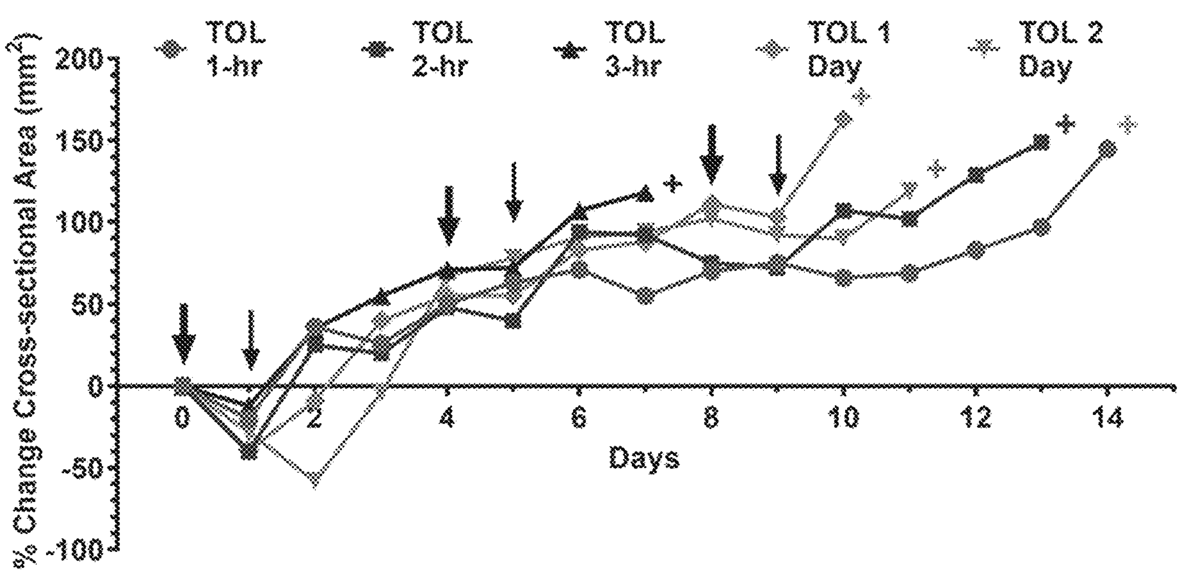
FIG. 14 illustrates the growth of 4T1 homografts in female BALBc mice receiving TOL with different stimulus durations.

FIG. 14 illustrates the growth of 4T1 homografts in female BALBc mice that were treated with TOL using different stimulus durations. Groups (n=8) 1, 2 and 3 received hourly injections of digoxin (3 mg/kg) on Day 0 to achieve and maintain steady-state levels of drug through the exposure to PEFs (18 V/m, 10 ms positive/negative ramp, 15 interstimulus intervals) for a total of 1, 2 or 3 hours of stimulation. This procedure was repeated on Day 4. Group 4 received 8 injections of digoxin on Days 0, 4 and 8 to achieve and maintain steady-state levels through 4×30-minutes exposures to PEF stimulation for a single treatment day. Group 5 was similarly treated but per routine, received treatment on 2 successive days that also began on Days 0, 4 and 8. All treatment protocols were observed to reduce the size of homografts from baseline after the first day of treatment. This response was greater if a second treatment was provided on the following day. There was no significant difference noted between the groups of mice exposed to 1, 2 or 3 hours of PEF stimulation on a single day. Plus signs (+) denote the day all mice in a group met humane endpoint euthanasia criteria. No clear pattern of difference in mouse survival was observed. The optimum safe and effective treatment protocol for TOL is to achieve and maintain a steady-state level of digoxin through 2 hours of PEF stimulation for 2 successive days.

The electric fields produced by the present invention may also have other therapeutic or industrial applications.

It is to be understood that the above described embodiments are merely illustrative of numerous and varied other embodiments which may constitute applications of the principles of the invention. Such other embodiments may be readily devised by those skilled in the art without departing from the spirit or scope of this invention and it is our intent they be deemed within the scope of our invention.

EXAMPLES

The following examples, including the experiments conducted and results achieved are provided for illustrative purposes only and are not to be construed as limiting upon the present invention.

Example 1. Large Animal Trial Treatments with Targeted Osmotic Lysis

Based on consistent results of in vivo trials with experimental animals revealing that targeted osmotic lysis (TOL), without adverse behavioral effects or damage to normal tissues, was able to consistently reduce the size of ectopic xenografts by 30-50% and extend the survival of host mice by an average of 10-14 days compared to control-treated mice, trial treatments were initiated in two dogs using the present coaxial ring device after extensive safety testing was performed on normal cats and dogs.

Dog 1 is a 12-year-old female Labrador retriever with 2 tumors in the right lung. She failed to respond chemotherapy. An X-ray of the chest was obtained and a tissue sample from the tumor was obtained and processed immunocytochemically to determine the level of voltage-gated sodium channel (VGSC) expression. It was found that the level of VGSC expression was sufficiently high to recommend treatment and to indicate that a positive response to treatment would be anticipated. Pre-treatment with digoxin was initiated to attain steady-state levels of drug. On the days of treatment, the dog received one additional dose of digoxin and was then exposed to pulsed electric field (PEF) stimulation in the coaxial ring device at an 18 V/m field amplitude. She was then sent home and returned the next day for a second period of stimulation. The dog showed no signs of discomfort during treatment and no signs of adverse cognitive or behavioral effects were observed by the owner. A post-treatment X-ray of the chest revealed an approximate 17-20% reduction in size of each tumor. Based on the initial response to treatment, a second round of treatment was administered. No adverse effects were noted during the treatment. It was noted that the dog's appetite had increased and her activity level increased significantly. One month later, the dog received a third round of treatment, but was noted to be experiencing gastrointestinal upset, with mental "dullness" and lethargy. She was examined and samples were taken for laboratory testing which revealed a moderate elevation in BUN/creatinine. She was placed on steroids. The dog's condition continued to decline so the decision was made to euthanize. Based upon laboratory tests and the clinical presentation, the reason for the sudden decline was not likely related to tumor lysis syndrome associated with treatment, but to metastatic spread of the cancer to the brain.

Dog 2 is a 15-year-old male Labrador retriever with 2 tumors in the right lung. He failed to respond chemotherapy. An X-ray of the chest was obtained and a tissue sample from the tumor was obtained and processed immunocytochemically to determine the level of voltage-gated sodium channel (VGSC) expression. It was found that the level of VGSC expression was sufficiently high to recommend treatment and to indicate that a positive response to treatment would be anticipated. Pre-treatment with digoxin was initiated to attain steady-state levels of drug. On the days of treatment, the dog received one additional dose of digoxin and was then exposed to pulsed electric field (PEF) stimulation in the coaxial ring device at an 18 V/m field amplitude for 2 hours. He was then sent home and returned the next day for a second period of stimulation. The dog showed some anxiety about getting into the carrier, but no signs of discomfort during treatment and no signs of adverse cognitive or behavioral effects. A post-treatment X-ray of the chest revealed an approximate 25% reduction in size of each tumor. Based on the initial response to treatment, a second round of treatment was administered. No adverse effects were noted during or after the treatment. The tumor continued to decrease in size but the amount of tumor reduction seemed to be slightly less with each treatment. No significant behavior change had been noted. A third round of treatment was administered using a smaller, bench-size coaxial ring device. The treatment parameters were the same as before, but due to this dog's level of anxiety, a single dose of acepromazine was administered prior to being placed within the bore of the device. The procedure was well tolerated. A pre-treatment X-ray was not obtained before the treatment, but comparison of the post-treatment X-ray of the chest in the third round treatment to the post-treatment X-ray obtained in the second round treatment revealed a variable, but overall a reduction in tumor size of approximately 5%. This finding was considered significant because the tumors would have been expected to grow during the period between the second treatment and third treatment.

The dog was treated for the fourth time using the bench-sized coaxial ring device with the same field strength of 18 V/m for 2 hours on two consecutive days. The dog received post-treatment X-ray and the tumors were found to be stable and slightly smaller than they were after the third round treatment. The dog has now completed four courses of treatment in three months and the tumors are smaller than they were when first imaged. His owner reported that his behavior and appetite remained about the same and that there have been no serious side effects, except from sedation.

In sum, these findings suggest that targeted osmotic lysis may provide a safe and effective treatment for advanced stage carcinomas in large animals without compromising the patient's quality of life.

Example 2. Emergency Use Treatment of a Human Patient with Pulsed Electric Field Generator The patient was in the fifth decade of life with refractory cancer of the cervix. The patient's clinical issues included intractable pain even on high dose narcotics on a PCA pump, and failure to thrive. Patient was on hydromorphone, morphine, methadone, and anxiolytics. Multiple manipulations of the pain medications had not yielded any relief. The patient's ECOG Performance Status was a 4. The patient's tumor was considered refractory to all standard of care treatments and the patient was not eligible for any local clinical trial. Given the patient's extreme distress due to tumor progression, the patient was considered for targeted osmotic lysis (TOL) treatment as an emergency use because patient's previously performed biopsy showed increased expression of sodium channels.

Patient was started on digoxin with the following dosage: 0.25 mg on Day 1; 0.5 mg on Day 2; 0.25 mg on Day 3; 0.25 mg on Day 4; 0.25 mg on Day 5. Prior to stimulation, patient underwent safety tests for CBC, CMP, uric acid, digoxin levels and a EKG rhythm strip. The patient also received IV fluids and allopurinol.

The patient was then placed in the coaxial ring device that delivered pulsed electric fields (18 V/m field amplitude, a 10 ms positive/negative ramp and a 15 ms interstimulus interval). To obviate any possible adverse interaction between the pulsed electric fields, test stimulation periods of 15-30 sec were administered starting at 2 (the lowest field strength), 4, 6, 8, 10, 12, 14, 16 and 18 V/m (the treatment field strength). The patient reported no perception of discomfort. Treatment then was provided at 18 V/m for a total of two hours with breaks at 15-minute intervals to check for blood pressure and heart rate.

Post-treatment laboratory test samples and a post-treatment EKG strip were obtained. No issues were noted in the observation period post treatment. Patient was given another 1 liter of saline in anticipation of tumor lysis. The patient appeared to have tolerated the procedure well.

The patient's spouse monitored the patient's blood pressure, urine output and temperature at home. It was reported that the patient experienced mild temperature elevation to 101 degrees in the evening that responded to treatment with acetaminophen. The patient experienced high levels of pain during the night, which required additional doses of the patient's breakthrough analgesic regimen. The quality and distribution of the pain was the same as that reported prior to undergoing treatment with TOL.

The patient returned for the second session of the two-day protocol on the next day. Pretreatment laboratory samples and an EKG rhythm strip were obtained. The patient was again treated in the coaxial ring device at 18 V/m for two hours, with breaks to check blood pressure and heart rate.

The patient's labs were stable except for the hemoglobin that fell to a low of 6.4 grams. This was thought to be hemodilution. The patient was not transfused.

The patient's spouse reported that the patient experienced a fever of 101.9 degrees that was reduced to 100.7 degrees with oral acetaminophen on the second night. The patient continued to produce urine the output of which was measured twice at 50 ccs then 30 ccs. The patient's pain did not spike after the second round of stimulation and the patient was noted to be up and walking around the house "in short spurts", more than usual.

On the second day post treatment, the patient had labs done which showed the patient's hemoglobin had returned to the patient's baseline of 7.1 grams. All other labs continued at baseline.

On the third day post treatment, the patient has returned to home hospice care. The patient was reported to be more ambulatory and afebrile. Pain persisted and the patient's dose of narcotics had been increased. The patient was more interactive and could carry on a reasonably long conversation. The most marked change has been the patient's appetite which had improved significantly. The objective measurements of tumor density revealed that the tumor density decreased from 70 to 56 HU 3 days post-treatment and further decreased to 47 HU 20 days post-treatment.

The patient had experienced 2 episodes of mild hemorrhagic anal discharge, but the patient reported no dizziness. The patient's blood pressure had been steady 89-102/60-63 and the patient's nurse reported that the patient's color was better.

LIST OF REFERENCE SIGNS

1 Ring structure
2 Electrostatic ring unit
3 Cable
4 A driving and sensing circuitry
5 Microprocessor

The invention claimed is:

1. A method for therapeutic treatments via targeted osmotic lysis, comprising administering to a subject pulsed electric fields generated by a device for generating pulsed electric fields, comprising an electrostatic ring unit comprising a driving and sensing circuitry and a plurality of ring structures positioned along the longitudinal axis, wherein the ring structures are made of an electrically conductive material, and wherein the driving and sensing circuitry is configured to charge the ring structures to different voltage levels, wherein the pulsed electric fields are administered at an 18 V/m field amplitude for 2 hours for two successive days.

2. The method of claim 1, further comprising administering the pulsed electric fields monthly to a subject with a tumor until the tumor is clinically undetectable.

3. The method of claim 1, further comprising administering the pulsed electric fields monthly to a subject with a tumor over the course of the subject's lifetime.

4. A method for therapeutic treatments via targeted osmotic lysis, comprising administering to a subject pulsed electric fields generated by a device for generating pulsed electric fields, comprising an electrostatic ring unit comprising a driving and sensing circuitry and a plurality of ring structures positioned along the longitudinal axis, wherein the ring structures are made of an electrically conductive material, and wherein the driving and sensing circuitry is configured to charge the ring structures to different voltage levels, wherein the pulsed electric fields are administered for two successive days and further comprising administering to the subject digoxin, wherein there is a digoxin free period between each 2-day administration of pulsed electric fields.

5. The method of claim 4, wherein the digoxin free period between each 2-day administration of pulsed electric fields is at least 5 days.

6. The method of claim 4, wherein the digoxin free period between each 2-day administration of pulsed electric fields is about two to four weeks.

* * * * *